United States Patent
Parthangal et al.

(10) Patent No.: US 8,324,703 B2
(45) Date of Patent: Dec. 4, 2012

(54) APPROACH TO CONTACTING NANOWIRE ARRAYS USING NANOPARTICLES

(75) Inventors: Prahalad Parthangal, Galthersburg, MD (US); Michael R. Zachariah, Potomac, MD (US); Richard E. Cavicchi, Washington Grove, MD (US)

(73) Assignees: University of Maryland, College Park, MD (US); The United States of America as represented by the Secretary of Commerce, Washington, DC (US)

( * ) Notice: Subject to any disclaimer, the term of this patent is extended or adjusted under 35 U.S.C. 154(b) by 571 days.

(21) Appl. No.: 12/111,696

(22) Filed: Apr. 29, 2008

(65) Prior Publication Data

US 2009/0032801 A1    Feb. 5, 2009

Related U.S. Application Data

(60) Provisional application No. 60/914,801, filed on Apr. 30, 2007.

(51) Int. Cl.
*H01L 31/107* (2006.01)
(52) U.S. Cl. .................. 257/438; 257/419; 257/E51.04; 438/57; 977/773; 977/762
(58) Field of Classification Search ............. 438/57, 438/47, 209; 257/419, 414, 438
See application file for complete search history.

(56) References Cited

U.S. PATENT DOCUMENTS

| | | | | |
|---|---|---|---|---|
| 7,872,318 | B2 * | 1/2011 | Stewart et al. | 257/414 |
| 8,210,994 | B2 * | 7/2012 | Chang et al. | 482/83 |
| 2005/0009224 | A1 * | 1/2005 | Yang et al. | 438/57 |
| 2006/0138575 | A1 * | 6/2006 | Kamins | 257/419 |

* cited by examiner

*Primary Examiner* — Jerome Jackson, Jr.
*Assistant Examiner* — Fang-Xing Jiang
(74) *Attorney, Agent, or Firm* — Carter, DeLuca, Farrell & Schmidt, LLP

(57) ABSTRACT

An in situ approach toward connecting and electrically contacting vertically aligned nanowire arrays using conductive nanoparticles is provided. The utility of the approach is demonstrated by development of a gas sensing device employing the nanowire assembly. Well-aligned, single-crystalline zinc oxide nanowires were grown through a direct thermal evaporation process at 550° C. on gold catalyst layers. Electrical contact to the top of the nanowire array was established by creating a contiguous nanoparticle film through electrostatic attachment of conductive gold nanoparticles exclusively onto the tips of nanowires. A gas sensing device was constructed using such an arrangement and the nanowire assembly was found to be sensitive to both reducing (methanol) and oxidizing (nitrous oxides) gases. This assembly approach is amenable to any nanowire array for which a top contact electrode is needed.

17 Claims, 6 Drawing Sheets

APPROACH TO CONTACTING NANOWIRE ARRAYS USING NANOPARTICLES

PRIORITY

The present application claims priority to a U.S. provisional patent application filed on Apr. 30, 2007 and assigned U.S. Provisional Patent Application Ser. No. 60/914,801, the contents of which are incorporated herein by reference.

This invention was made with government support under Contract Number 70NANB3H1140 awarded by the National Institute of Standards and Technology. The government has certain rights in the invention.

BACKGROUND

Despite significant advancements in nanowire growth techniques and device descriptions, establishment of electrical contacts to nanowire assemblies through non-destructive methods has not been successfully realized. The commonly employed method involves physically removing nanowires from the sample, dispersing them in solution, and transferring them onto another surface containing probe pads, and depositing contact electrodes onto individual nanowires through some form of lithography. Such a series of steps are not only destructive, but also expensive and tedious.

Another method described in the literature involves burying the nanowire array in an insulating matrix such as spin-on glass or polystyrene, followed by plasma etching to expose the nanowire tips. However, this approach prevents access to the surface of the nanowires, which would be necessary for applications like gas sensing.

SUMMARY

The present disclosure is directed to a vertically aligned nanowire assembly and a gas sensing device having said assembly. The present disclosure is also directed to a method for growing electrodes in situ in contact with the top of the vertically aligned nanowire assembly by selectively attaching gold nanoparticles to the tips of nanowires and forming a continuous film. The electric field enhancements around the sharp tips of nanowires as well as their high aspect ratios are exploited in this procedure, which is generic to a wide range of nanomaterials and nanostructures. The result is a device which is an ensemble of single nanowire devices connected in parallel.

For sensor applications there may be signal-to-noise advantages in such an arrangement compared to single nanowire devices. Prior art nanowire-based sensors have involved disordered nanowire networks, where electrical contact is determined primarily by the contacts between individual nanowires. In contrast, the properties of the device according to the present disclosure reflect the electrical transport along isolated nanowires. The method according to the present disclosure may also be suitable for applications other than sensors, such as, for example, for electrically driven optical devices based on nanowires.

It is envisioned that the nanowire assembly in accordance with the present disclosures can be suitable for applications other than sensing, such as gas sensing, applications. Therefore, the gas sensing device in accordance with the present disclosure having the nanowire assembly is one specific application of the nanowire assembly.

Additionally, the method described herein toward electrically contacting the top of an aligned nanowire array using a conductive nanoparticle film can be employed for nanotube arrays.

DETAILED DESCRIPTION

In the present disclosure the term nanowire is defined as an electrically conductive nanorod; alternatively, a wire with a diameter of nanometer dimensions. The term nanoparticle is defined as structure having three dimensions of 100 nm or less. The term nanotube is defined as a fullerene molecule having a cylindrical or toroidal shape.

A nanowire assembly of zinc oxide (ZnO), owning its great potential in the development of new electronic and photonic devices, was grown and studied. ZnO is a wide-bandgap semiconductor ($E_g$=3.37 eV) with a wurtzite crystal structure that has been grown into several morphologies including nanowires, nanocombs, nanobelts, nanorings and nanoribbons, etc. through both gas-phase and solution-phase syntheses. One-dimensional ZnO nanowires have been observed to act as gas sensors, room temperature ultraviolet (UV) lasing cavities, UV/visible photodetectors and field effect transistors. Synthesis of well-aligned nanowire arrays of ZnO is of prime importance for the realization of nanoelectronic devices such as light emitting diodes (LEDs) and laser diodes. Several groups have synthesized ZnO nanowires by simple thermal evaporation of commercial Zn and ZnO powders. Metal-organic chemical vapour deposition (MOCVD) of ZnO nanorods has also been described using precursors like diethyl zinc and zinc acetylacetonate hydrate.

In accordance with the present disclosure, nanowire arrays of ZnO on gold (Au) catalyst layers deposited on silicon dioxide ($SiO_2$) substrates were grown, through direct thermal evaporation of Zn powder within a tube furnace maintained at about 550° C. The nanowires were found to be well aligned and vertically oriented, with an average diameter of 60-75 nm and had faceted, hexagonal heads, with a growth direction along the c-axis.

EXPERIMENTAL SECTION

Growth of ZnO Nanowire Arrays

Figure 1:
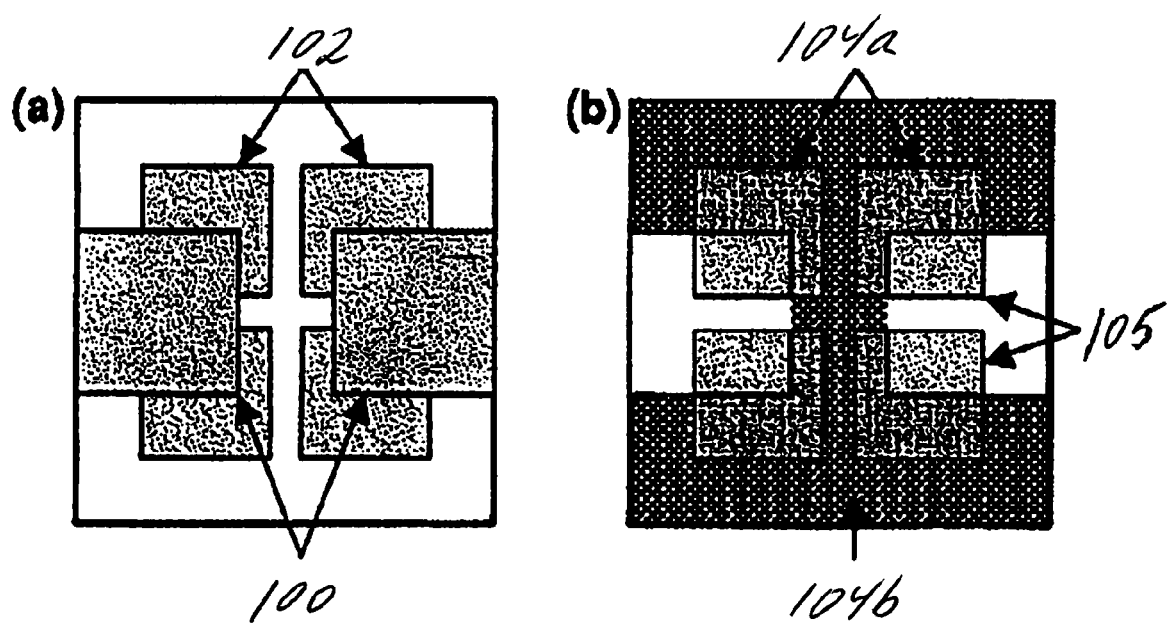
FIGS. 1(a) and 1(b) represent substrate surfaces before and after nanowire growth, respectively. Clean $SiO_2$ wafers were placed on top of the substrate before nanowire growth to enable electrical contact to the bottom of the nanowires grown on each individual catalyst pad.

Silicon dioxide wafers (1 cm$^2$) 100 (see FIG. 1(*a*)) were ultrasonically cleaned in acetone and four square pads 102 of 15 nm of chromium (Cr) followed by 150 nm of gold (Au) were deposited (Cr was deposited to ensure better adhesion of Au to the substrate). The substrates were then placed in an alumina boat containing commercial Zn powder (Aldrich, 99.5%), and loaded into a quartz tube placed within a horizontal tube furnace, the substrates being held 5 cm downstream of the Zn powder. The tube was then evacuated using a rotary mechanical vacuum pump, and this was followed by the introduction of 150 sccm (standard cubic centimeters per minute) nitrogen ($N_2$) and 10 sccm oxygen ($O_2$) and brought back up to atmospheric pressure.

The nanowires 104*a*, 104*b* were grown at about 550° C. for about two hours and the substrates were then cooled down to room temperature. A schematic diagram of the substrate surface before and after nanowire growth is shown in FIGS. 1(*a*) and 1(*b*). The unexposed Au layers 105 are shown in FIG. 1(*b*).

Nanoparticle Generation and Deposition

Au nanoparticles were generated through an aerosol spray-pyrolysis method. A 0.03 M (mol l$^{-1}$) aqueous solution of hydrogen tetrachloroaurate ($HAuCl_4$; Sigma Aldrich Inc.) was sprayed into droplets with an atomizer, using a carrier gas flow of 2 slpm (standard liters per minute) $N_2$. The flow containing the droplets was passed through silica gel dehumidifiers, and then into a tube furnace maintained at 600° C., to thermally crack the precursor and form Au particles. The particles were then positively charged with a homebuilt unipolar charger and introduced into a electrostatic precipitator containing the substrate with the grown nanowire arrays of ZnO. A high negative electric field of −10 kV cm$^{-1}$ was applied to drive the particle deposition.

Nanowire Characterization and Gas Sensing Measurements

The morphology of the substrates was imaged using a Hitachi S-4000 scanning electron microscope (SEM). Wide-angel x-ray diffraction (XRD) patterns were recorded on a Siemens D-500 diffractometer using Cu Kα radiation, while transmission electronic microscopy (TEM) and selected area electron diffraction were performed using a Zeiss CM 10 microscope.

For gas sensing measurements, the sample was glued onto a large square package containing pin contacts for electrical connections using a high temperature adhesive paste (Ceramabond 503; Aremco Products Inc., NY). Wire bonds were attached to all four gold pads 102 for resistance measurements. Controlled mass flow rates of test gases and zero-grade dry air were delivered through a computer-automated delivery system, to the sample that was placed on a temperature-programmable hotplate. Fixed temperature responses of the nanowire array (at 325° C.) to various concentrations (10-50 ppm-parts per million by volume or μl l$^{-1}$) of methanol ($CH_3OH$) and nitrous oxide ($NO_x$) were measured and analysed.

Results and Discussion

Morphology and Crystallography of ZnO Nanowire Arrays

Figure 2:
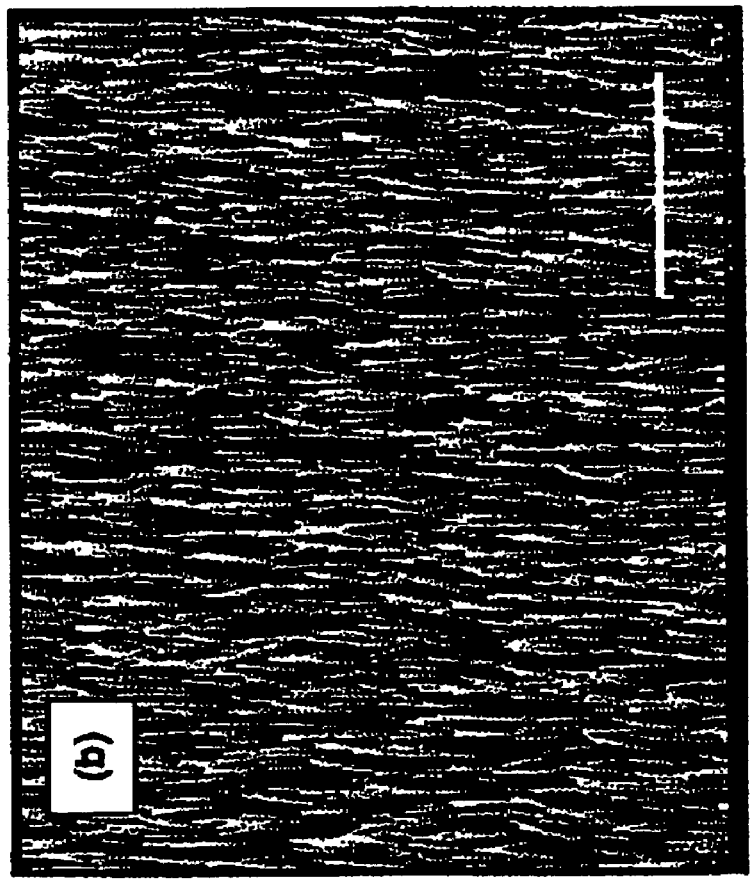
FIG. 2(a) is an SEM image of ZnO nanowires on Au and $SiO_2$ (left and right portions) clearly indicate alignment of nanowires on Au and lack of alignment on $SiO_2$.
FIG. 2(b) is a more magnified SEM image at the well-aligned nanowire array of ZnO on Au. Scale bars for (a) and (b) are 10 μm and 3.75 μm, respectively.
Figure 2:
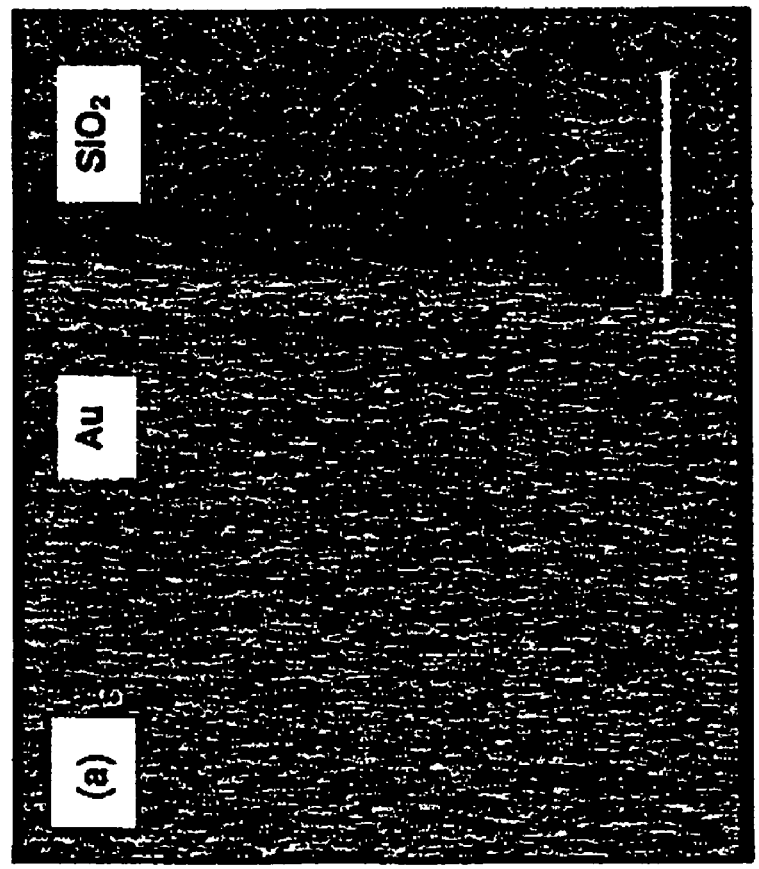

SEM images of the ZnO nanowires are presented in FIG. 2. The nanowires 104*a* grown on the Au catalyst layer are well aligned along the vertical direction with widths between 60 and 80 nm, and lengths between 5 and 10 μm, while the nanowires 104*b* on the adjacent $SiO_2$ portion are more randomly oriented.

In a typical XRD pattern obtained from the nanowires, the sharp peak at a 2-theta value of 34.42° corresponds to the (0 0 2) plane of the hexagonal ZnO crystal. TEM and electron diffraction analysis of individual nanowires revealed that the nanowires are single crystalline, with a growth direction along the c-axis of ZnO. The growth mechanism for the nanowires on Au 104*a* generally follows a vapour-liquid-solid (VLS) mechanism, wherein Zn vapour is transported and reacted with the Au catalyst, forming alloy droplets which provide nucleation sites for ZnO vapours to condense and grow into well-crystallized nanowires. Growth on $SiO_2$ generally follows a non-catalytic vapour-solid (VS) mechanism, in which zinc and zinc suboxides condense on the $SiO_2$ surface to form droplets which act as nuclei for ZnO nanowire growth.

Nanoparticle Film Contact Description and I-V Characteristics of ZnO Nanowire Array Even though nanowire arrays of various materials have been routinely synthesized and studied, there has been surprisingly little progress in the development of methods for electrically contacting them as grown, i.e., without removing them from the substrate. In accordance with the present disclosure, a technique has been developed for achieving electrical contacts to both ends of nanowire array 200 (FIG. 4) using the Au catalyst layer 202 as the bottom electrode, and an Au nanoparticle film 204 as the top electrode. The nanoparticles were attracted onto the nanowire arrays using a high electric field, as described in the experimental section above. The bottom electrode 202 is provided on a $SiO_2$ substrate 205.

Figure 3:
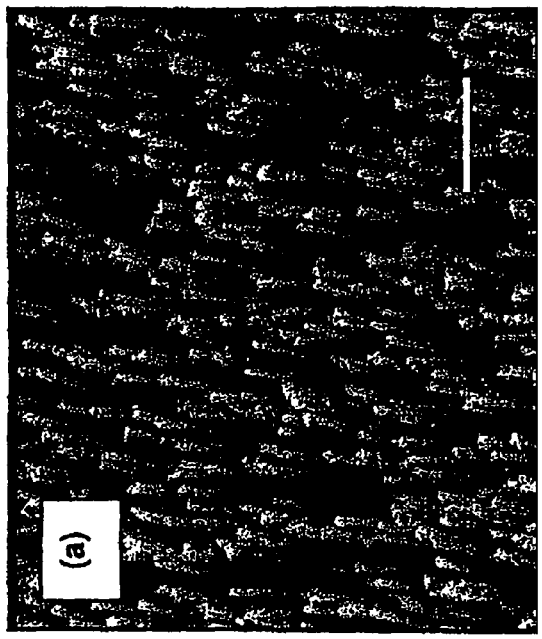
FIGS. 3(a)-(c) show SEM images of Au nanoparticles attached to the tips of nanowires at different stages of deposition—(a) 10 min, (b) 1 hour, and (c) 2 hours. Scale bars=1 μm.
Figure 3:
Figure 3:
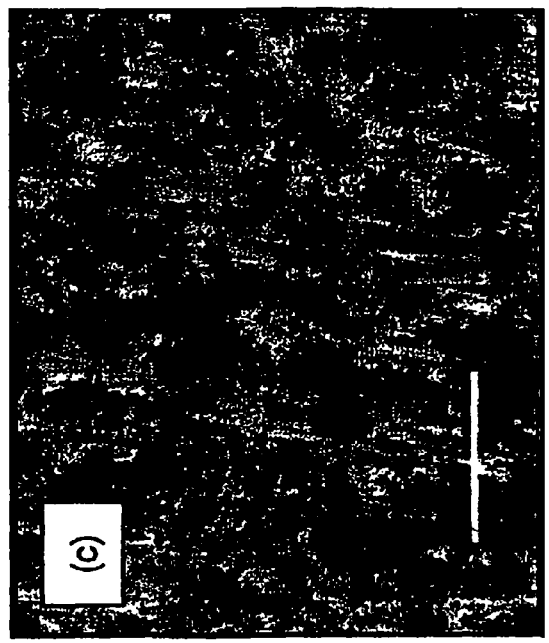

The key aspect of the high field deposition is that the regions near the tips of the nanowires have the highest field and result in particle collection only at the top of the nanowires. SEM images of Au nanoparticles deposited on the nanowire assembly 300 for different deposition times are shown in FIG. 3, and confirm that particles only deposit on the ends of the nanowires and subsequently branch out to begin to form a continuous film at larger deposition times. Typically, particle depositions were carried out for two hours in order to create a continuous film of Au.

Figure 4:
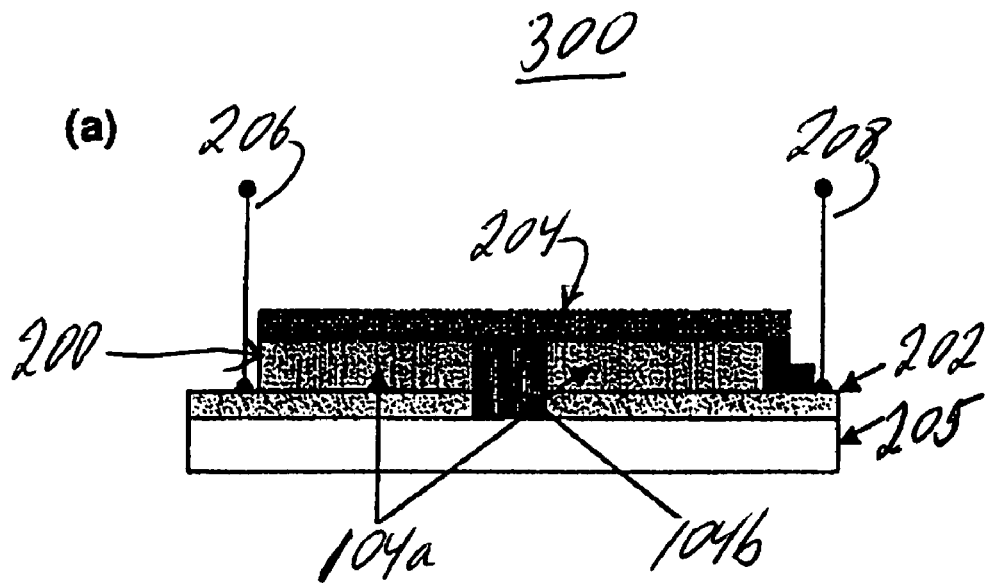
FIG. 4(a) is a schematic diagram of electrical contacts to the nanowire array.
FIG. 4(b) is a graph showing the I-V characteristic of the nanowire array measured in air.
Figure 4:
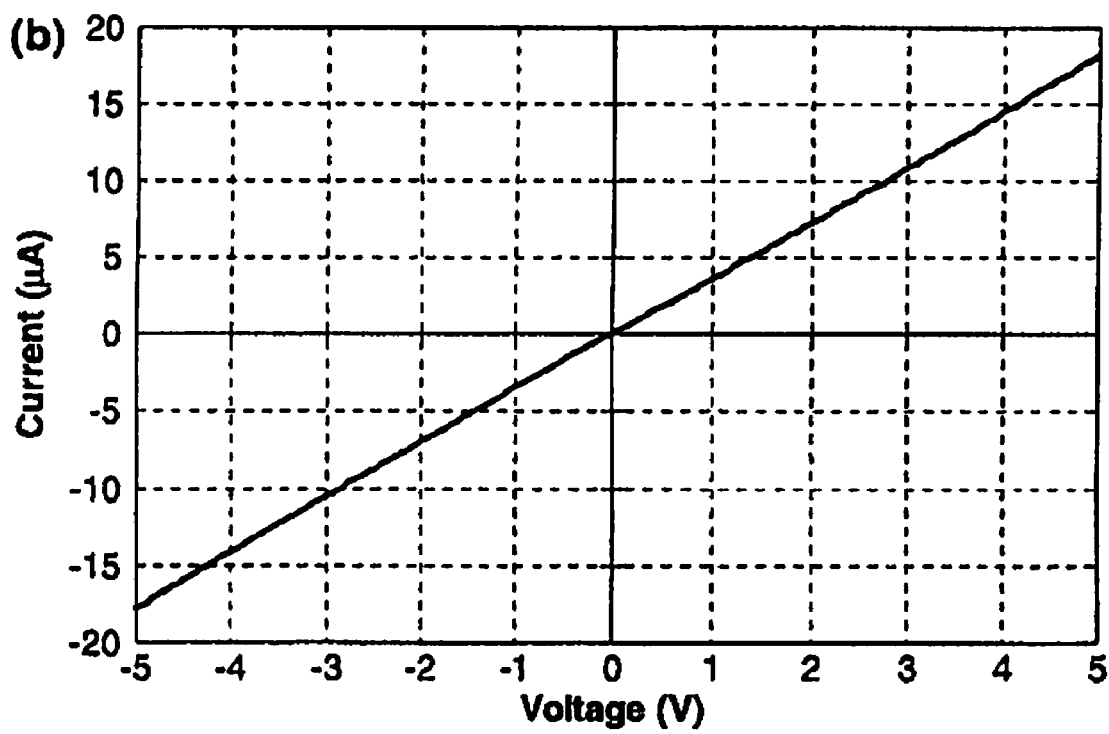

A probe station was used to measure resistances between various points on the same contact electrode to verify film continuity, and between the top and bottom contacts 208, 206 to measure the nanowire array resistance. Before nanowire growth, electrical isolation between the various pads 102 of Cr/Au was confirmed. Following nanowire growth and nanoparticle film deposition, both the underlying and overlying Au layers were verified to be conducting, and there was no visible shorting between the bottom and top electrodes 204, 202. Typically, the Au nanoparticle film 204 was deposited such that it made contact with two of the four gold pads 102, thereby enabling simple electrical continuity verification. A representative diagram of the electrodes 202, 204 contacting the ends of the nanowire array 200 is shown in FIG. 4(*a*). I-V characteristics of the nanowire array 200 in air were measured and averaged for different bias voltages applied between the two contacts 206, 208 indicating good contact between the nanowires and nanoparticles, as seen in FIG. 4(*b*). These results confirmed that the approach or method to create a top contact for nanowire arrays using a nanoparticle aerosol source was successful.

Gas Sensing Properties of the ZnO Nanowire Arrays

Semiconducting metal oxides such as tin oxide ($SnO_2$), titanium dioxide ($TiO_2$) and zinc oxide (ZnO) have been widely utilized as active materials in solid-state gas sensing devices. In particular, ZnO surfaces with a variety of morphologies including thin films, flakes and nanowires have been tested for the detection of gases including ethanol, carbon monoxide, hydrogen sulphide, oxygen and nitrous oxides. Due to their very high surface to volume ratio, nanowires present an attractive alternative to thin films for improved gas sensing characteristics, including sensitivity and overall speed of response.

As a first practical test of the nanowire assembly approach/method according to the present disclosure, it was demonstrated in the implementation of a gas sensing device. In the past, as-grown nanowire arrays could not be used for gas sensor testing, possibly due to difficulties in achieving a continuous top contact to the nanowires using standard approaches like thermal evaporation, without interfering with the ability of the analytes to interact with the sensing material (nanowires). The technique according to the present disclosure for attaching electrodes 202, 204 to nanowire arrays 200 could solve this vexing problem since the nanoparticle film 204 is a porous but electrically continuous electrode, allowing gases to come into contact and absorb onto the nanowires 104a, 104b both from the sides as well as the top.

Figure 5:
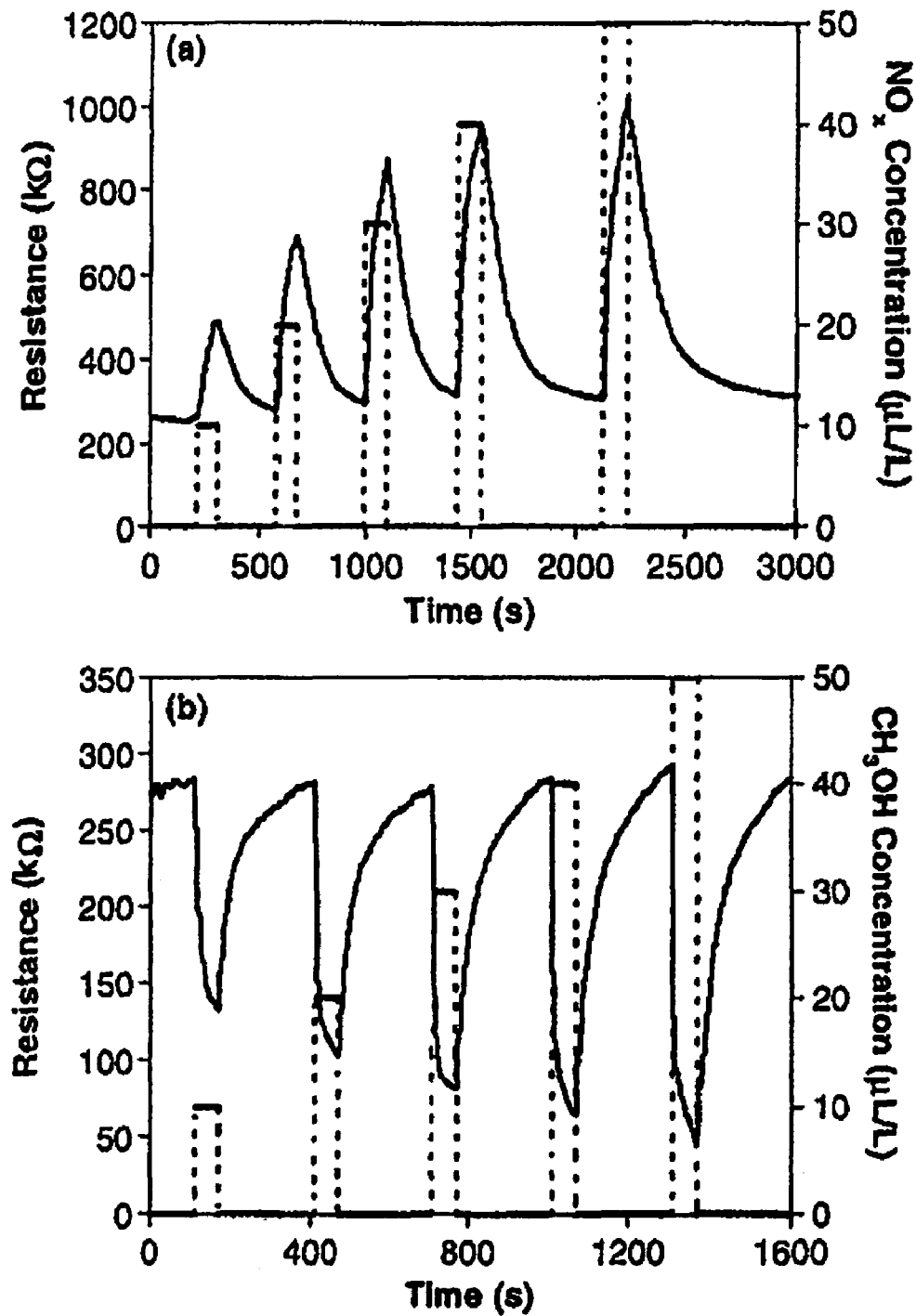
FIGS. 5(a) and (b) are graphs showing gas sensing responses of the nanowire array to pulsed concentrations of nitrous oxides and methanol (10-50 ppm), respectively, in air at 325° C.

Typically, the sample was initially annealed in air at 300° C. for over eight hours, and the stability of the electrodes on the device was evaluated at various temperatures. Fixed temperature responses of the nanowire assembly 300 to pulsed concentrations (10-50 ppm) of methanol ($CH_3OH$) and nitrous oxides ($NO/NO_2$) were measured at 325° C., and are shown in FIG. 5. As expected, the resistance of the ZnO nanowires increased upon exposure to the oxidizing analyte, $NO_x$, and reduced or decreased upon exposure to the reducing analyte, $CH_3OH$. The sensor response clearly tracks the pulsed input of the analyte. However, the recovery time for the sensor to re-attain its original resistance was somewhat high, possibly due to slow desorption rates.

Figure 6:
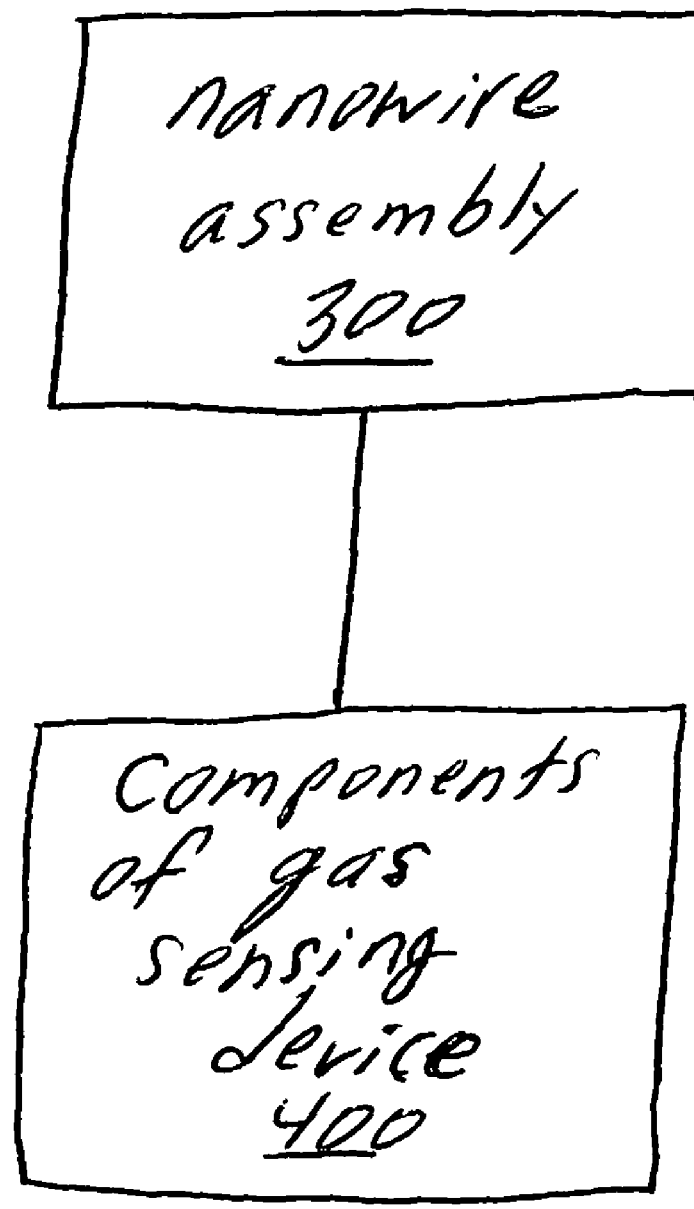
FIG. 6 is a block diagram of a gas sensing device having the nanowire assembly in accordance with the present disclosure.

The continuity of the contact layers as well as sensor responses were found to be remarkably stable and reproducible for repeated testing cycles and the sensitivities were comparable to an existing ZnO nanowire-based sensor. While the gas sensing device 250 using the nanowire assembly shown by FIG. 4(a), and other components 400 indicative of gas sensing devices, such as a processor, audible alarm, display, etc. (see FIG. 6), is still in a primitive state, it does demonstrate the efficacy of the nano-assembly approach/method according to the present disclosure.

CONCLUSIONS

In summary, an original, generic approach or method toward achieving electrical contacts to vertically aligned ZnO nanowire arrays using electrostatically assisted deposition of Au nanoparticles was devised and tested. The Au nanoparticle electrode is observed to be both mechanically and electrically robust even at high temperatures. This approach of creating a top contact to a vertically aligned nanowire assembly as grown, may be useful for the design and fabrication of electrically driven nanowire lasers and LEDs. The first successful application of this nanowire assembly or architecture shown by FIG. 4(a) and according to the present disclosure is a gas sensing device, which exhibits high sensitivities to low concentrations (10 ppm to 50 ppm) of both reducing (methanol) and oxidizing (nitrous oxide) gases.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A sensing device comprising:
 a nanowire assembly comprising:
 a nanowire array having a plurality of vertically aligned nanowires;
 a first electrode having an electrically continuous porous film formed by a plurality of nanoparticles, the film in electrical contact with a respective tip of a nanowire of the plurality of vertically aligned nanowires; and
 a second electrode opposite said first electrode and in contact with said plurality of vertically aligned nanowires.

2. The sensing device according to claim 1, further comprising another nanowire array having a plurality of non-vertically aligned nanowires adjacent to said nanowire array having the plurality of vertically aligned nanowires.

3. The sensing device according to claim 1, further comprising a substrate in contact with said second electrode.

4. The sensing device according to claim 3, wherein the substrate is an $SiO_2$ substrate.

5. The sensing device according to claim 1, wherein said plurality of nanowires are ZnO nanowires and said plurality of nanoparticles are Au nanoparticles.

6. The sensing device according to claim 1, wherein said plurality of nanowires are ZnO nanowires whose resistance increases upon exposure to an oxidizing analyte and decreases upon exposure to a reducing analyte.

7. The sensing device according to claim 1, wherein the nanoparticle film is an Au nanoparticle film.

8. The sensing device according to claim 1, wherein the second electrode is formed of a continuous catalyst layer.

9. A nanowire assembly comprising:
 a nanowire array having a plurality of vertically aligned nanowires; and
 an electrode having an electrically continuous porous film formed by a plurality of nanoparticles, the film in electrical contact with a respective tip of a nanowire of the plurality of vertically aligned nanowires,
 wherein the electrically continuous porous film enables a gas to pass through the film and surround the nanowire array.

10. The assembly according to claim 9, further comprising another nanowire array having a plurality of non-vertically aligned nanowires adjacent to said nanowire array having the plurality of vertically aligned nanowires.

11. The assembly according to claim 9, further comprising a substrate in contact with a catalyst layer positioned opposite a nanoparticle film formed by said plurality of nanoparticles.

12. The assembly according to claim 9, wherein said plurality of nanowires are ZnO nanowires and said plurality of nanoparticles are Au nanoparticles.

13. The assembly according to claim 9, wherein said plurality of nanowires are ZnO nanowires whose resistance increases upon exposure to an oxidizing analyte and decreases upon exposure to a reducing analyte.

14. The assembly according to claim 9, further comprising a continuous catalyst layer positioned opposite a nanoparticle film formed by said plurality of nanoparticles and in contact with said plurality of vertically aligned nanowires.

15. The assembly according to claim 9, wherein the vertically aligned nanowires are formed using a Vapour-Liquid-Solid mechanism.

16. The assembly according to claim 9, wherein the plurality of nanoparticles are charged and selectively deposited onto the tips of the vertically aligned nanowires.

17. The assembly according to claim 16, wherein the selection of the tips for the depositing is achieved by applying a high electric field during the depositing.

* * * * *